United States Patent
DeBruler et al.

(10) Patent No.: US 8,712,573 B2
(45) Date of Patent: *Apr. 29, 2014

(54) SYSTEMS AND METHODS FOR CONTROLLING REGISTRATION OF ADVANCING SUBSTRATES IN ABSORBENT ARTICLE CONVERTING LINES

(75) Inventors: Jason L. DeBruler, West Chester, OH (US); Andrew P. Palmer, Lebanon, OH (US); Louis J. Cedrone, Mason, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 127 days.

This patent is subject to a terminal disclaimer.

(21) Appl. No.: 13/402,251

(22) Filed: Feb. 22, 2012

(65) Prior Publication Data

US 2012/0150332 A1 Jun. 14, 2012

Related U.S. Application Data

(63) Continuation of application No. 12/476,348, filed on Jun. 2, 2009, now Pat. No. 8,145,343.

(51) Int. Cl.
*G06F 19/00* (2011.01)
(52) U.S. Cl.
USPC ........... 700/124; 700/122; 700/125; 700/126; 226/9; 226/10; 356/429
(58) Field of Classification Search
USPC .......... 700/122, 124–126; 226/9–10; 356/429
See application file for complete search history.

(56) References Cited

U.S. PATENT DOCUMENTS

| 5,286,543 | A | 2/1994 | Ungpiyakul et al. |
| 5,359,525 | A | 10/1994 | Weyenberg |
| 5,980,087 | A * | 11/1999 | Brandon et al. ............... 700/125 |
| 6,450,321 | B1 | 9/2002 | Blumenthal et al. |
| 6,705,453 | B2 | 3/2004 | Blumenthal et al. |

(Continued)

FOREIGN PATENT DOCUMENTS

| EP | 1 528 907 B1 | 9/2008 |
| WO | WO 2007/105938 A1 | 9/2007 |

(Continued)

OTHER PUBLICATIONS

Ken Harris, "An Application of IEEE 1588 to Industrial Automation," Rockwell Automation Publication 1756-WP005A-En-E, Jan. 2009.

(Continued)

*Primary Examiner* — Ramesh Patel
(74) *Attorney, Agent, or Firm* — Charles R. Matson

(57) ABSTRACT

The present disclosure relates to systems and processes for controlling the registration of advancing substrates in absorbent article converting lines. The systems and methods may utilize feedback from technologies, such as vision systems, sensors, remote input and output stations, and controllers with synchronized embedded clocks to accurately correlate registration feature detections and substrate speed control on an absorbent article converting process. The systems and methods may accurately apply the use of precision clock synchronization for both instrumentation and control system devices on a non-deterministic communications network. In turn, the clock synchronized control and instrumentation network may be used to control the substrate speed. As such, the controller may be programmed to track registration features on substrates and components along the converting line without having to account for undeterminable delays.

7 Claims, 7 Drawing Sheets

(56) References Cited

U.S. PATENT DOCUMENTS

| | | | |
|---|---|---|---|
| 6,764,563 B2* | 7/2004 | Henry et al. | 156/64 |
| 6,801,828 B2 | 10/2004 | Popp et al. | |
| 6,811,019 B2 | 11/2004 | Christian et al. | |
| 6,814,217 B2 | 11/2004 | Blumenthal et al. | |
| 6,820,022 B2 | 11/2004 | Popp et al. | |
| 6,829,516 B2 | 12/2004 | Popp et al. | |
| 6,845,278 B2 | 1/2005 | Popp et al. | |
| 6,888,083 B2* | 5/2005 | Hergeth | 209/576 |
| 6,909,106 B2* | 6/2005 | Ungpiyakul et al. | 250/559.4 |
| 7,082,347 B2* | 7/2006 | Popp et al. | 700/125 |
| 7,123,981 B2 | 10/2006 | Dollevoet et al. | |
| 7,162,319 B2* | 1/2007 | Popp et al. | 700/110 |
| 7,171,283 B2* | 1/2007 | Popp et al. | 700/121 |
| 7,187,995 B2* | 3/2007 | Floeder et al. | 700/122 |
| 7,797,133 B2* | 9/2010 | Floeder et al. | 702/183 |
| 7,882,438 B2* | 2/2011 | Markham et al. | 715/736 |
| 7,982,764 B2* | 7/2011 | Kadaba | 348/61 |
| 8,145,338 B2* | 3/2012 | Kent et al. | 700/110 |
| 8,145,343 B2* | 3/2012 | DeBruler et al. | 700/124 |
| 8,145,344 B2* | 3/2012 | DeBruler et al. | 700/125 |
| 2003/0169424 A1* | 9/2003 | Vogt et al. | 356/429 |
| 2004/0019400 A1* | 1/2004 | Popp et al. | 700/125 |
| 2004/0022426 A1* | 2/2004 | Carbone et al. | 382/141 |
| 2004/0030432 A1* | 2/2004 | Popp et al. | 700/109 |
| 2004/0083018 A1 | 4/2004 | Dollevoet et al. | |
| 2004/0089516 A1* | 5/2004 | Christian et al. | 198/459.8 |
| 2005/0043841 A1* | 2/2005 | Popp et al. | 700/110 |
| 2005/0125180 A1* | 6/2005 | Miller et al. | 702/94 |
| 2005/0154485 A1* | 7/2005 | Popp et al. | 700/124 |
| 2005/0217791 A1* | 10/2005 | Costello et al. | 156/277 |
| 2006/0047705 A1* | 3/2006 | Reade et al. | 707/104.1 |
| 2008/0132865 A1* | 6/2008 | Li et al. | 604/378 |
| 2008/0223537 A1* | 9/2008 | Wiedmann | 162/198 |
| 2010/0305738 A1* | 12/2010 | DeBruler et al. | 700/105 |
| 2012/0150331 A1* | 6/2012 | DeBruler et al. | 700/108 |
| 2012/0150332 A1 | 6/2012 | DeBruler et al. | |
| 2012/0150336 A1 | 6/2012 | Kent et al. | |

FOREIGN PATENT DOCUMENTS

| | | |
|---|---|---|
| WO | WO 2007/126345 A1 | 11/2007 |
| WO | WO 2007/126347 A1 | 11/2007 |
| WO | WO 2012/125526 A1 | 9/2012 |

OTHER PUBLICATIONS

"Precision clock synchronization protocol for networked measurement and control systems," IEEE 1588, First edition, 2004.

Dopplinger et al., "Aligning System Clocks Over Networks With IEEE 1588 Remote Timing Standard," Analog Zone, 2006.

Pastorius et al., "High-speed tire inspection," Tire Technology International, 2007, pp. 149-150.

http://zone.ni.com/devzone/cda/tut/p/id/2822; "Introduction to Distributed Clock Synchronization and the IEEE 1588 Precision Time Protocol," May 14, 2008, pp. 1-6.

http://www.automation.com/smc/print.php?stripImages=no; "Today's Automation News Headlines from Automation.com," Dec. 16, 2008.

Paul G. Schreier, http://www.entrepreneur.corn/tradejournals/article/print/197678918.html, "IEEE 1588 to transform timing synchronization," Entrepreneur; Apr. 2009, pp. 1-6.

PCT International Search Report dated Sep. 17, 2010, 15 pages.

U.S. Appl. No. 12/476,479, filed Jun. 2, 2009—Office Action mailed Aug. 15, 2011, (8 pages).

U.S. Appl. No. 12/476,533, filed Jun. 2, 2009—Office Action mailed Aug. 17, 2011, (7 pages).

U.S. Appl. No. 13/402,205, filed Feb. 22, 2012—Office Action mailed Aug. 12, 2013, (8 pages).

U.S. Appl. No. 13/402,233, filed Feb. 22, 2012—Office Action mailed Aug. 27, 2011 (10 pages).

* cited by examiner

SYSTEMS AND METHODS FOR CONTROLLING REGISTRATION OF ADVANCING SUBSTRATES IN ABSORBENT ARTICLE CONVERTING LINES

CROSS REFERENCE TO RELATED APPLICATION

This application is a continuation of U.S. patent application Ser. No. 12/476,348, filed Jun. 2, 2009, now U.S. Pat. 8,145,343 which is hereby incorporated by reference.

FIELD OF THE INVENTION

The present disclosure relates to systems and methods for manufacturing disposable absorbent articles, and more particularly, systems and methods for controlling the registration of advancing substrates in absorbent article converting lines.

BACKGROUND OF THE INVENTION

Along an assembly line, diapers and various types of other absorbent articles may be assembled by adding components to and otherwise modifying an advancing, continuous web of material. For example, in some processes, advancing webs of material are combined with other advancing webs of material. In other examples, individual components created from advancing webs of material are combined with advancing webs of material, which in turn, are then combined with other advancing webs of material. Once the desired component parts are assembled, the advancing web(s) and component parts are subjected to a final knife cut to separate the web(s) into discrete diapers or other absorbent articles. The discrete diapers or absorbent articles may also then be folded and packaged.

In some manufacturing operations, a continuous base web of material is advanced in a machine direction along a converting line. Discrete components and continuous webs are combined with the base web of material to form a continuous length of absorbent articles. As such, it may be necessary to accurately control the speed the base web to help ensure that the final knife cut is applied at desired locations to ensure the desired pitch length of the articles is maintained. As such, some registration control systems may utilize registration marks on the base web to determine if the base web is properly positioned with respect to the final knife. Registration marks may be configured in different ways. For example, in some instances, registration marks may be in the form of graphics printed on the base web. As the base web advances, the registration marks pass by a sensor that detects the presence the registration marks. The sensor provides a feedback signal that corresponds to when a registration mark is detected. A controller receives the feedback signal from the sensor and compares the feedback signal with a setpoint. Based on the comparison, the controller may change the speed of the base web.

At relatively low base web speeds, the registration control system may have adequate time to accurately change the web speed in response to feedback signals from the sensor. However, at relatively high base web speeds, time delays within registration control system may result in unstable and/or inaccurate control of base web speed. In turn, unstable and/or inaccurate base web speed control may result in misplaced final knife cuts on the continuous length of absorbent articles, resulting in damaged and/or defective absorbent articles. There may be various sources of time delays within the registration control system, such as time delays associated with the sensor and/or control loops. Some systems may attempt to compensate for the time delays by requiring the converting line to operate at relatively low base web speeds, which results in relatively lower production rates. Other systems may attempt to compensate for the time delays by utilizing high speed sensors, which may add to the complexity and cost of the manufacturing operation. Still other systems may attempt to compensate for the time delays by directly wiring the sensor input into a servo controller to control the base web speed.

SUMMARY OF THE INVENTION

The present disclosure relates to systems and processes for controlling the registration of advancing substrates in absorbent article converting lines. The systems and methods may utilize feedback from technologies, such as vision systems, sensors, remote input and output stations, and controllers with synchronized embedded clocks to accurately correlate registration feature detections and substrate speed control on an absorbent article converting process. The systems and methods may accurately apply the use of precision clock synchronization for both instrumentation and control system devices on a non-deterministic communications network. In turn, the clock synchronized control and instrumentation network may be used to control the substrate speed. As such, the controller may be programmed to track registration features on substrates and components along the converting line without having to account for undeterminable delays.

In one form, a method for registering absorbent products from a web converting manufacturing process includes the steps of: providing a communication network; connecting a sensor with the communication network, the sensor including a sensor clock; connecting a controller with the communication network, the controller including a controller clock; synchronizing the sensor clock with the controller clock such that the reported time of the controller clock and the sensor clock are correlated; advancing a substrate in a machine direction through a converting process at a first speed, the substrate including registration features arranged along the machine direction; providing a machine axis that generates counts that correspond with locations along machine direction; assigning a timestamp to each count, wherein each timestamp is based on the controller clock; detecting the registration features with the sensor; communicating registration feature detections from the sensor to the communication network; assigning a timestamp to each registration feature detection, wherein each timestamp is based on the sensor clock; sequentially adding component parts to the substrate; receiving the registration feature detections and corresponding timestamps from the communication network into the controller; comparing the timestamps of the registration feature detections with the timestamps of the count data; adjusting the first speed of the substrate based on the comparison of the timestamps associated with the registration feature detections with the timestamps associated with the count data; cutting the substrate with component parts added thereto into discrete absorbent articles; and packaging the discrete absorbent articles.

In another form, a method for registering absorbent products from a web converting manufacturing process includes the steps of: providing a communication network; connecting a sensor with the communication network, the sensor including a sensor clock; connecting a controller with the communication network, the controller including a controller clock; synchronizing the sensor clock with the controller clock such that the reported time of the controller clock and the sensor clock are correlated; advancing a first substrate in a machine direction through a converting process at a first speed, the substrate including registration features arranged along the machine direction; advancing a second substrate in the machine direction through a converting process at a second speed; providing a machine axis that generates counts that correspond with locations along machine direction; assigning a timestamp to each count, wherein each timestamp is based on the controller clock; detecting the registration features with the sensor; communicating registration feature detections from the sensor to the communication network; assigning a timestamp to each registration feature detection, each timestamp based on the sensor clock; combining the first substrate with the second substrate; receiving the registration feature detections and corresponding timestamps from the communication network into the controller; comparing the timestamps of the registration feature detections with the timestamps of the counts; adjusting the second speed based on the comparison of the timestamps associated with the registration feature detections with the timestamps associated with the counts; cutting or placing the first substrate and second substrate combined therewith into discrete absorbent articles; and packaging the discrete absorbent articles.

DETAILED DESCRIPTION OF THE INVENTION

Figure 1:
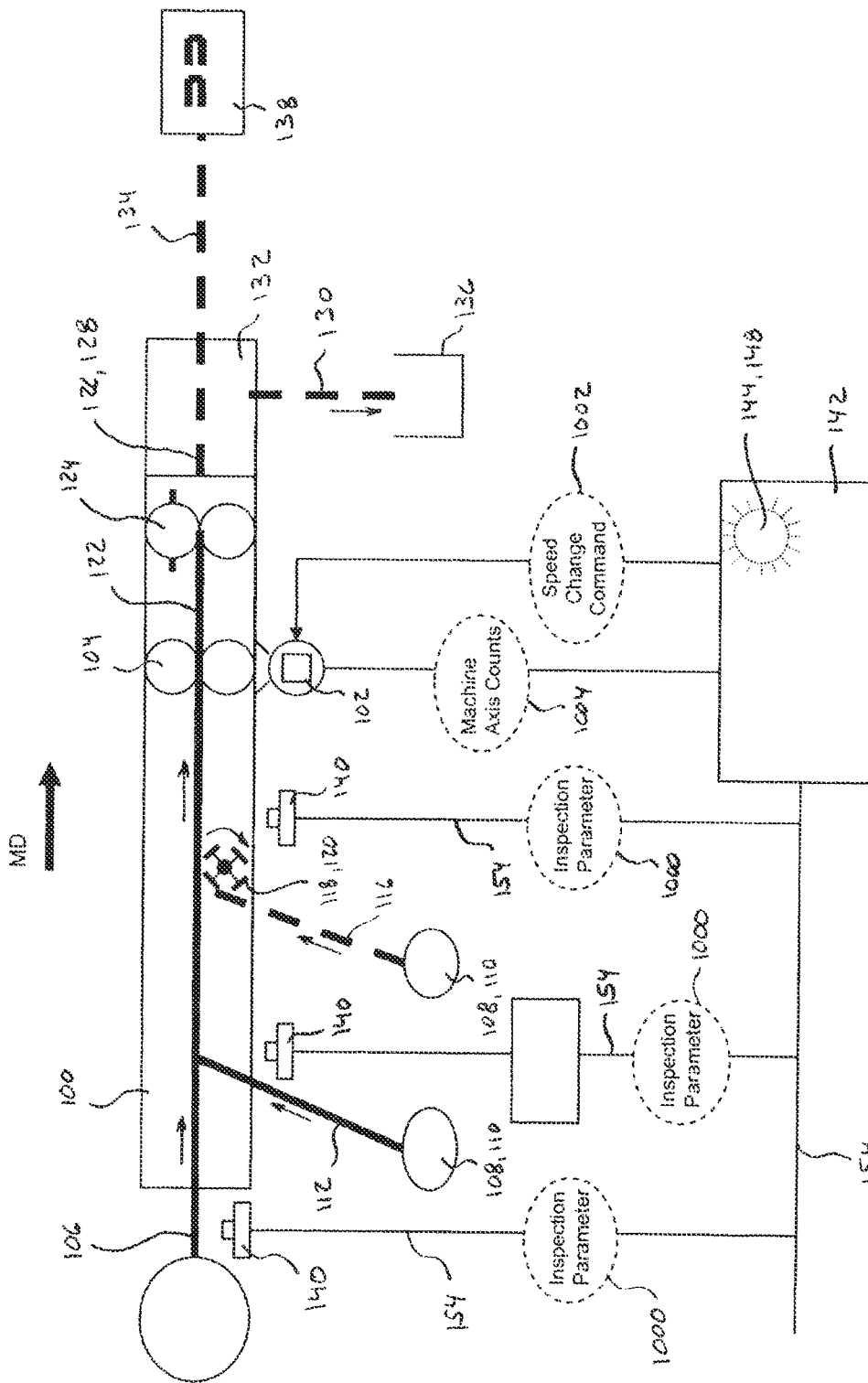
FIG. 1 is a schematic representation of an absorbent article converting line and reject system.

The following term explanations may be useful in understanding the present disclosure:

"Absorbent article" is used herein to refer to consumer products whose primary function is to absorb and retain soils and wastes. "Diaper" is used herein to refer to an absorbent article generally worn by infants and incontinent persons about the lower torso. The term "disposable" is used herein to describe absorbent articles which generally are not intended to be laundered or otherwise restored or reused as an absorbent article (e.g., they are intended to be discarded after a single use and may also be configured to be recycled, composted or otherwise disposed of in an environmentally compatible manner).

The term "disposed" is used herein to mean that an element(s) is formed (joined and positioned) in a particular place or position as a macro-unitary structure with other elements or as a separate element joined to another element. As used herein, the term "joined" encompasses configurations whereby an element is directly secured to another element by affixing the element directly to the other element, and configurations whereby an element is indirectly secured to another element by affixing the element to intermediate member(s) which in turn are affixed to the other element. The term "substrate" is used herein to describe a material which is primarily two-dimensional (i.e. in an XY plane) and whose thickness (in a Z direction) is relatively small (i.e. $1/10$ or less) in comparison to its length (in an X direction) and width (in a Y direction). Non-limiting examples of substrates include a layer or layers or fibrous materials, films and foils such as plastic films or metallic foils that may be used alone or laminated to one or more web, layer, film and/or foil. As such, a web is a substrate. The term "nonwoven" refers herein to a material made from continuous (long) filaments (fibers) and/or discontinuous (short) filaments (fibers) by processes such as spunbonding, meltblowing, and the like. Nonwovens do not have a woven or knitted filament pattern. The term "machine direction" (MD) is used herein to refer to the direction of material flow through a process. The term "cross direction" (CD) is used herein to refer to a direction that is generally perpendicular to the machine direction.

The present disclosure relates to systems and processes for controlling the registration of advancing substrates in absorbent article converting lines. In particular, the systems and methods herein focus on creating a more accurate registration control system with improved set-up, registration feature detection, tracking, and validation algorithms. For example, the systems and methods may utilize feedback from technologies, such as vision systems, sensors, remote input and output stations, and controllers with synchronized embedded clocks to accurately correlate registration feature detections and substrate speed control on an absorbent article converting process. As such, the systems and methods may accurately apply the use of precision clock synchronization for both instrumentation and control system devices on a non-deterministic communications network, such as for example, an EthernetIP network. In turn, the clock synchronized control and instrumentation network may be used to control the substrate speed. As such, the controller may be programmed to track registration features on substrates and components along the converting line without having to account for undeterminable delays. In addition, the controller may be programmed to virtually divide the substrate along the machine direction MD into virtual segments based on the speed of the substrate and anticipated clock inaccuracies.

Although the present disclosure is provided in the context of manufacturing absorbent articles, and diapers in particular, it is to be appreciated that the systems and methods disclosed herein may be applied to the manufacture of various types of articles and products involving the monitoring of various different types of substrates and/or components. Examples of other products include absorbent articles for inanimate surfaces such as consumer products whose primary function is to absorb and retain soils and wastes that may be solid or liquid and which are removed from inanimate surfaces such as floors, objects, furniture and the like. Non-limiting examples of absorbent articles for inanimate surfaces include dusting sheets such as the SWIFFER cleaning sheets, pre-moistened wipes or pads such as the SWIFFER WET pre-moistened cloths, paper towels such as the BOUNTY paper towels, dryer sheets such as the BOUNCE dryer sheets and dry-cleaning clothes such as the DRYEL cleaning clothes all sold by The Procter & Gamble Company. Additional examples of products include absorbent articles for animate surfaces whose primary function is to absorb and contain body exudates and, more specifically, devices which are placed against or in proximity to the body of the user to absorb and contain the various exudates discharged from the body. Non-limiting examples of incontinent absorbent articles include diapers such as PAMPERS diapers, training and pull-on pants such as PAMPERS FEEL 'N LEARN and EASY UPS, adult incontinence briefs and undergarments such as ATTENDS adult incontinence garments, feminine hygiene garments such as panty liners, absorbent inserts, and the like such as ALWAYS and TAMPAX, toilet paper such as CHARMIN toilet paper, tissue paper such as PUFFS tissue paper, facial wipes or clothes such as OLAY DAILY FACIAL wipes or clothes, toilet training wipes such as KANDOO pre-moistened wipes, all sold by The Procter & Gamble Company. Still other examples of products include packaging components and substrates and/or containers for laundry detergent and coffee, which may be produced in pellets or pouches and may be manufactured in a converting or web process or even discreet products produced at high speed such as high-speed bottling lines or cosmetics. Still other examples of products include a web substrate containing labels to be placed on bottles and/or containers for laundry detergent (such as Tide, Gain, etc.), fabric enhancers (such as Febreeze, Downy, etc.), hair and beauty care products (such as Head & Shoulders, Old Spice deodorant/antiperspirant, Herbal Essence, Pantene, etc.), and cleaning products (such as Mr. Clean, Cascade, Dawn, Ivory, etc.). Further, it is to be appreciated that although the present disclosure often refers to monitoring or viewing substrates and/or webs, it is to be appreciated that the registration systems discussed herein can be used to monitor and/or view combinations of webs and individual components as well as parts added as a continuous web of material and parts added as a discontinuous web of material.

FIG. 1 shows a schematic representation of an absorbent article converting process including a converting line or machine 100 configured to manufacture diapers. It is to be appreciated that the systems and methods disclosed herein are applicable to work with various types of converting processes and/or machines. As shown in FIG. 1, the converting line 100 may include one or more motors 102 that drive transport systems, such as a nip roll 104, to move diaper substrates and component materials through the manufacturing process. For example, FIG. 1 shows for example, a base substrate 106 and two auxiliary substrates and/or components 108 of material used to construct portions of the diapers. The substrates may be provided as rolls and fed into the converting line 100. It is to be appreciated that material of the auxiliary substrates may be supplied in various ways. For example, FIG. 1 shows a first auxiliary substrate 110 in the form of a continuous substrate 112, and a second auxiliary substrate 114 in the form of individual components 116. It is to be appreciated that the auxiliary substrates 110 may be transferred to the base substrate 106 through various types of transfer mechanisms. For example, the individual components 116 are shown as being transferred to the base substrate via a transfer mechanism 118 in the form of a servo patch placer mechanism 120, such as disclosed in U.S. Pat. Nos. 6,450,321; 6,705,453; 6,811,019; and 6,814,217. It is also to be appreciated that the various substrates can be used to construct various components of the absorbent articles, such as backsheets, topsheets, absorbent cores, front and/or back ears, fastener components, and various types of elastic webs and components such as leg elastics, barrier leg cuff elastics, and waist elastics. Exemplary descriptions of absorbent article components are provided below with reference to FIG. 7. Referring back to FIG. 1, as the base substrate 106 advances through the converting line 100, the base substrate 106 is combined with the auxiliary substrates 108 and/or discrete components 116 to create a continuous length of absorbent articles 122. At a downstream portion of the converting process 100, the continuous length of absorbent articles 122 is subjected to a final knife 124 and cut to create separate and discrete absorbent articles 126 in the form of diapers 128. As discussed in more detail below, a registration control system may be used to ensure that final knife is applied to cut the diapers in desired locations.

As shown in FIG. 1, defective articles 130 may be subject to a rejection system 132 and removed from the process. For example, FIG. 1 shows defective diapers 130 being channeled to a reject bin 136. Diapers 134 that are not deemed to be defective may be subject to further processing steps, such as folding and packaging. For example, FIG. 1 shows non-defective diapers advancing from the final knife to a folding mechanism 138. In some embodiments, a pneumatic system may be used to remove defective absorbent articles from the assembly line. More particularly, after application of the final knife and before being folded by a folding mechanism, defective articles are removed from the assembly line by a blast of compressed air discharged from the pneumatic system. In other embodiments, defective articles may be allowed to advance from the final knife, partially through a folding mechanism, and into a reject bin. Such a system, described for example in U.S. Patent Publication No. US20080223537A1, may stop or slow the motion of tucker blades on the folding mechanism such that a rejected article will pass through a portion of the folding mechanism without being folded and fall into a reject bin. After the defective articles have passed through the folding mechanism, motion of the tucker blades is resumed, allowing the tucker blades to engage non-defective articles and causing the non-defective articles to be folded and channeled toward a packaging process downstream of the folding mechanism.

As shown in FIG. 1 and as described in more detail below, various sensors 140 and other devices may be arranged adjacent the converting line 100 may communicate with a controller 142. Based on such communications, the controller 142 may monitor and affect various operations on the converting line 100. As discussed in more detail below, the controller 142 may send speed change commands 1002 to the converter line 100 based on communications with the sensors 140. In the systems and methods described herein, the controller includes a computer system. The computer system may, for example, include one or more types of industrial programmable logic controller (PLC) and/or personal computer (PC) running software and adapted to communicate on an EthernetIP network. Some embodiments may utilize industrial programmable controllers such as the Siemens S7 series, Rockwell ControlLogix, SLC or PLC 5 series or Mitsubishi Q series. The aforementioned embodiments may use a personal computer or server running a control algorithm such as Rockwell SoftLogix or National Instruments Labview or may be any other device capable of receiving inputs from sensors, performing calculations based on those inputs and generating control actions through servomotor controls, electrical actuators or electro-pneumatic, electrohydraulic or other actuators.

As the substrates and components travel in the machine direction MD through the converting line, the controller tracks the advancement of the substrates and components. In some embodiments such as shown in FIG. 1, the controller 142 may track the advancement with counts generated by a machine axis 144 that correspond with machine direction positions on substrates and components while advancing though the converting line 100. In some configurations, the machine axis 144 may be configured as an actual motor 146 that provides count signals to the controller 142. The controller may utilize rotational speed, time, and/or count data from the machine axis 144 that correspond with the machine direction speed and travel of the substrates and components through the converting line.

It is to be appreciated that instead of or in addition to utilizing feedback from a physical machine axis as discussed above, the rotational motion of the machine axis 144 may be simulated by software in the controller. For example, in FIG. 1, the controller 142 can utilize counts generated by a virtual machine axis 148 in the controller software. More particularly, the virtual machine axis 148 may be programmed to imitate a motor that generates counts as the motor rotates. As such, it is to be appreciated that the machine axis referred to herein may be either a virtual axis existing in software or a physical axis corresponding with the rotational motion of a motor or other equipment.

Figure 2:
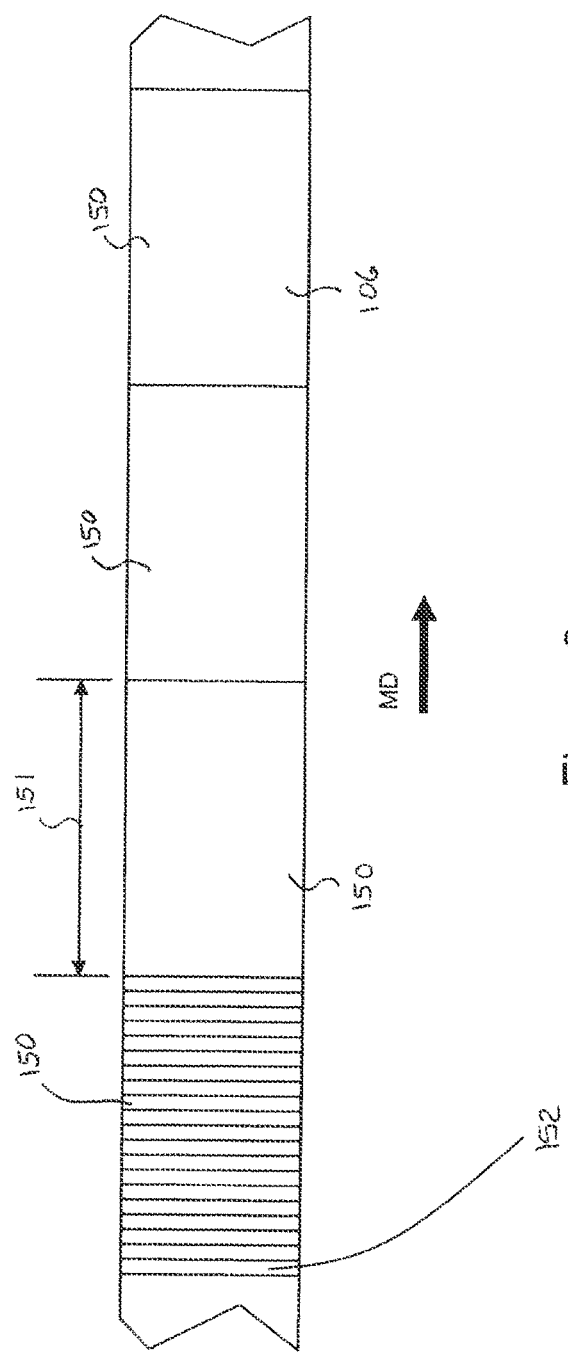
FIG. 2 is a top view of an advancing substrate showing virtual products and virtual segments.
Figure 7:
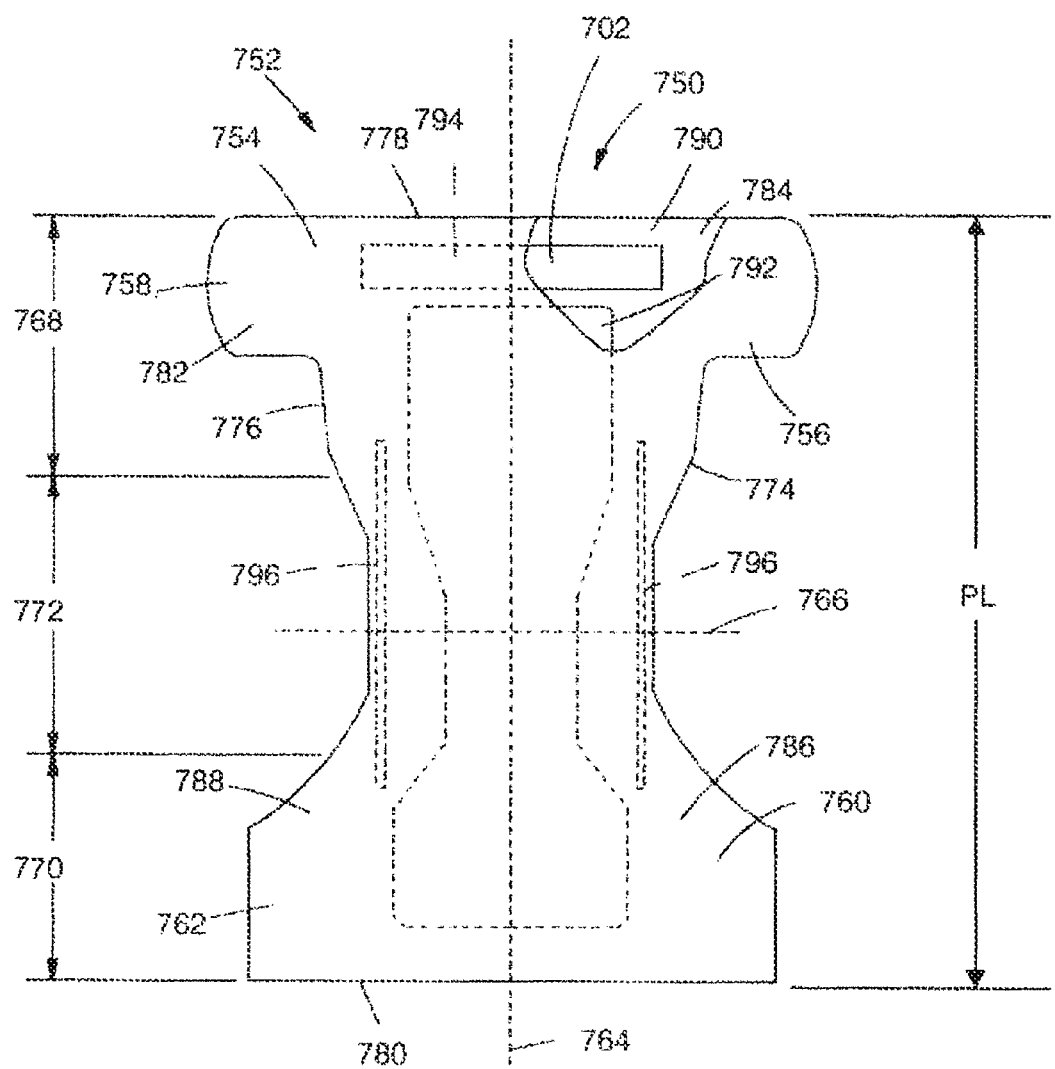
FIG. 7 is a top plan view of a disposable absorbent article that may include one or more substrates and/or components monitored and constructed in accordance with the present disclosure.

As discussed above, the machine axis may 144 be configured to correlate the linear motion of the substrates and components in the machine direction MD through the converting line 100 with counts corresponding with rotation of the machine axis 144. In some embodiments, one complete rotation of the machine axis 144 and associated count data correspond with one pitch length of an absorbent article 126. In some embodiments, the pitch lengths of the absorbent articles are the machine direction longitudinal lengths of the individual absorbent articles being produced. FIG. 7 shows an example of a longitudinal pitch length PL of a diaper. As such, the controller 142 may use counts generated from the machine axis 144 to virtually divide the substrates and components into virtual products 150. As shown in FIG. 2, the virtual products 150 may have machine direction lengths 151 that correspond with the pitch lengths of products being produced. For example, FIG. 2 shows a top side view of the base substrate 106 divided into virtual products 150 along the machine direction MD by the controller 142. Count signals corresponding with rotation of the machine axis that correspond with less than a complete rotation can also be used by the controller divide each virtual product 150 into virtual segments 152, such as shown in FIG. 2. As discussed in more detail below, the substrate speed and estimated clock inaccuracies can be used to determine the length of the each virtual segment in the machine direction MD, and in turn, the number of virtual segments in each virtual product. For example, FIG. 2 shows one virtual product 150 divided into twenty virtual segments 152. As discussed in more detail below, the controller 142 can also utilize signals from the inspection sensor 140 that corresponds with the detection of registrations features on the substrate, compare the feedback signals with count data from the machine axis, and adjust the speed of the substrate based on the comparison.

As previously mentioned, the systems and methods herein can utilize various types of sensors to monitor the substrates and components traveling through the converting line. As shown in FIG. 1, various types of inspection sensors 140 may be used to perform various functions. For example, inspection sensors 140 may be used to detect registration features, the relative placement of substrates and/or components, and various types of defects. As discussed in more detail below, based on the detections of the inspection sensors 140, feedback signals from the inspection sensors in the form of inspection parameters 1000 are communicated to the controller 142. For example, as shown and discussed in more detail below with reference to FIG. 3B, a sensor 140 can be configured to detect a registration feature 153 on a substrate and communicate an inspection parameter corresponding with the detection of the registration feature 153 to the controller 142. It is also to be appreciated that various types of controllers and inspection sensors can be configured in various ways to provide various types of data and perform various functions, for example, such as disclosed in U.S. Pat. Nos. 5,286,543; 5,359,525; 6,801,828; 6,820,022; and 7,123,981 and European Patent No. EP 1528907B1.

It is to be appreciated that various different types of inspection sensors 140 may be used to detect registration features 153 and monitor the substrates and components while advancing through the converting line 100. For example, inspection sensors 140 may be configured as photo-optic sensors that receive either reflected or transmitted light and serve to determine the presence or absence of a specific material; metal-proximity sensors that use electromagnetic to determine the presence or absence of a ferromagnetic material; capacitive or other proximity sensors using any of a number of varied technologies to determine the presence or absence materials. Inspection sensors 140 may also be configured as vision systems and other sub-processing devices to perform detection and, in some cases, logic to more accurately determine the status of an inspected product. Particular examples of inspections sensors 140 may include simple vision based sensors such as Cognex Checker series, integrated smart camera systems such as Cognex Insight, DVT Legend or Keyence smart cameras, component vision systems such as National Instruments CVS vision systems or PC based vision system such as Cognex VisionPro or any other vision system software which can run on a PC platform.

It should also be appreciated that inspection parameters 1000 corresponding with the detection of registration features may be provided from inspection sensors 140 in various forms. In one embodiment, inspection parameters 1000 may be in the form "results," such as for example, provided from a sensor state change resulting in a binary input corresponding with the detected presence or absence of a registration feature. In some embodiments, inspection parameters 1000 may be provided in the form of measurements and/or numerical indications of detected positions of registration features relative to components and/or substrates; and/or numerical indications of the positions of components and/or substrates relative to other physical or virtual references. In other embodiments, inspection parameters 1000 may be in the form of images transferred via a standard protocol such as ftp (File Transfer Protocol), DDE (Dynamic Data Exchange), or OPC (Object Linking and Embedding for Process Control). Thus, it is to be appreciated that various types of registration features 153 may be used with the systems and methods herein. Registration features 153 may include any signaling mechanism that is recognizable by a machine. For example, the registration features 153 may include a physical discontinuity such as notch, a protrusion, a depression, or a hole formed in a substrate and/or components. In some configurations, the registration features 153 may include a region of magnetic discontinuity, electrical discontinuity, electromagnetic discontinuity, and/or any combination thereof. Some registration features 153 may provide an optical marker that operates on the basis of providing detectable changes in intensities of visible and/or non-visible wavelengths of light. Various examples of registration features are provided in U.S. Pat. Nos. 5,286,543; 6,444,064; and 6,955,733. Registration features 153 may be configured to operatively indicate the boundaries between virtual products. In some configurations, the registration features 153 are regularly spaced at substantially equal intervals along machine direction of a substrate.

As shown in FIG. 3B, the registration features 153 are positioned adjacent lateral side edges of the first substrate 106.

As shown in FIG. 1, the inspection sensors 140 are connected with the controller 142 through a communication network 154, which allows the inspection sensors 140 to communicate inspection parameters 1000 to the controller 142. As discussed in more detail below, devices that communicate on the network each include precision clocks that are synchronized to a master clock within some specified accuracy. As shown in FIG. 1, the inspection sensors 140 and the controller 142 may be connected directly with the communication network 154. As such, each sensor or other field device connected directly with the communication network 154 may include a clock. Inspection sensors 140 that include a clock and that may be connected directly with the communication network 154 may include, for example, vision systems such as National Instruments PXI or any PC-based vision system such as Cognex VisionPro. Such sensors may also include other controllers that may be configured as peers to the controller or may be configured as subordinate to the controller.

In some embodiments, the inspection sensors 140 may be indirectly connected with the communication network 154. For example, the inspections sensors 140 may be connected with the communication network 154 through a remote input and output (I/O) station 156. When utilizing remote I/O stations 156, the inspection sensors 140 may be hardwired to the remote I/O stations, and in turn, the remote I/O stations 156 are connected with the communication network 154. As such, the each remote I/O station 156 may include a precision clock. Example remote I/O stations 156 or other IEEE-1588 based instruments that can be utilized with systems and methods herein include, for example a National Instruments PCI-1588 Interface (IEEE 1588 Precision Time Protocol Synchronization Interface) that synchronizes PXI systems, I/O modules and instrumentation over Ethernet/IP or a Beckhoff Automation EtherCat and XFC technology (eXtreme Fast Control Technology).

As previously mentioned, each device, such as the inspection sensors 140, remote I/O stations 156, and the controller 142, connected with the communication network 154 includes a clock, and each clock is synchronized to a master clock. In one configuration, the controller includes the master clock, referred to herein as a controller master clock, and all other clocks of devices connected with the communication network are referenced to the controller master clock. In such a configuration, the remote I/O stations and inspection sensors each include a clock, referred to herein as a sensor clock, which is synchronized to the controller master clock. Inspection parameters provided by the inspection sensors and communicated to the communication network are time-stamped with the time from the clocks on the corresponding sensors and remote I/O stations. In turn, the inspection parameters and corresponding timestamp data is sent to the controller over the communication network 154. Thus, the controller 142 can be programmed to evaluate the inspection parameter 1000 based on the actual time the inspection parameter was provided by the inspection sensor 140. Therefore, ambiguity as to when detections were actually made by an inspection sensor 140 is relatively small.

As previously mentioned, all clocks that are used to determine and report timestamps may be synchronized together. Clock synchronization allows the reported time from one device on the communication network 154 to be utilized by another device on the communication network. When the clocks are synchronized, ambiguity as to when an inspection parameter 1000 was actually provided by the inspection sensor 140 is affected only by the accuracy of the clocks with respect to each other. The clocks of the devices on the communication network may be synchronized in various ways depending on the type of communication network used.

In one embodiment, the communication network 154 is configured as a non-deterministic communication network, such as for example, Ethernet or Ethernet IP (industrial protocol) communication network. When using an Ethernet IP communication network, the clocks of each device may be synchronized using the IEEE1588 precision time protocol, described in IEEE1588 Standard, "Precision Clock Synchronization Protocol for Networked Measurement and Control Systems" and also described in Rockwell Automation publication number 1756-WPO05A-EN-E, published January 2009, and entitled "An Application of IEEE 1588 to Industrial Automation." As mentioned above, timestamps associated with inspection parameters from any inspection sensor may be referenced to the master clock, which allows the relative time as to when the inspection parameters were provided to be accurately calculated. In one configuration, the controller includes the master clock, the controller master clock, and all other clocks of devices connected with the communication network, the sensor clocks, are referenced to the controller master clock. As a result, the time as to when an inspection parameter was provided from an inspection sensor can be can be reported to the controller within the accuracy of an IEEE1588 compliant clock. In some embodiments, reported timestamps may be accurate to within 0.1 milliseconds of the controller master clock. In another configuration, another device, such as an Ethernet switch or router is the local master clock. In this case, both the controller clock and the sensor clock follow the local master clock. The identity of the local master is unimportant since all clocks in the system are synchronized to the local master within the IEEE1588 PTP standard.

With reference to the above description and figures, the methods and systems herein utilize a controller 142 and one or more inspection sensors 140 connected with a communication network 154. Each sensor 140, and remote I/O device 156, if used, have clocks that are synchronized with the master controller clock in the controller 142. The controller 142 tracks the movement of the substrates and components traveling in the machine direction of the converting line 100 and make speed adjustments thereto. More particularly, each count datum corresponds to expected machine direction positions of an advancing substrate, and the detection of registration features 153 correspond to the actual position of the advancing substrate. As such, the controller 142 compares expected substrate position with the actual substrate position, the controller adjusts the speed of the substrate accordingly. As discussed in more detail below, each count generated by the machine axis 144 includes an associated timestamp. In addition, the inspection sensors 140 provide inspection parameters 1000 indicating the detection of registration features to the controller via the communication network 154. As such, the sensors 140 provide inspection parameters 1000 to the communication network 154 along with associated timestamp from the sensor clocks. And the controller 142 compares the timestamps of the count data from the machine axis 144 with timestamps of inspection parameters indicating the detection of registration features 153. Based on the comparison, the controller 142 may send a speed change command 1002 to the converting line 100 to adjust the machine direction speed.

To provide additional context to the above discussion, the following provides a specific description of one example implementation of the systems and processes herein. FIGS. 3A-6B show an example of an absorbent article converting line 100 as substrates and components travel along the machine direction MD to a final knife cut 124 and a folding and/or packing system 138. In particular, FIGS. 3A, 4A, 5A, and 6A show schematic side views of the converting line 100, substrate 106, 108 and components 116, and FIGS. 3B, 4B, 5B, and 6B show top views of the substrates 106 and registration features 153 that correspond with FIGS. 3A, 4A, 5A, and 6A, respectively. For the purposes of the discussion relating to FIGS. 3A-6B, the converting line 100 is described in the context of a diaper converting line. In particular, a base substrate 106 having registration features 153 is shown to enter and advance in the machine direction MD through the converting line 100. Material from an auxiliary substrate 108 is cut into individual components 116, transferred and bonded to the base substrate 106 to form features 158 on the base substrate 106, such as for example, front ears on a diaper. FIGS. 3A, 4A, 5A, and 6A also show an inspection sensor 140, controller 142, machine axis 144, pad reject system 132, and folding system 138 associated with the converting line 100. In accordance with the above description, the machine axis 144 is shown schematically in the form of a virtual axis 148 provides base web position and speed signals to the controller 142. In turn, the controller 142 divides the base web into virtual products 150 along the machine direction MD. For the purposes of the present description, FIGS. 3A-6B show only three virtual products 150. Also in accordance with the above discussion, the inspection sensor 140 is connected with a remote I/O station 156. In turn, the remote I/O station 156 and controller 142 are connected with a communication network 154, in the form of an Ethernet IP network. It is to be appreciated that the more than inspection sensor 140 may be used and that some or all inspection sensors may be connected directly with the communication network 154 without using a remove I/O station. The remote I/O station includes a clock 1006, referred to herein as a sensor clock 1008 providing a time, Ts, and the controller includes a clock 1006, referred to herein as the master control clock 1010 providing a time, Tc. The sensor clock 1008 is synchronized with the master control clock 1010, such that Ts is set to equal Tc.

Figure 3:
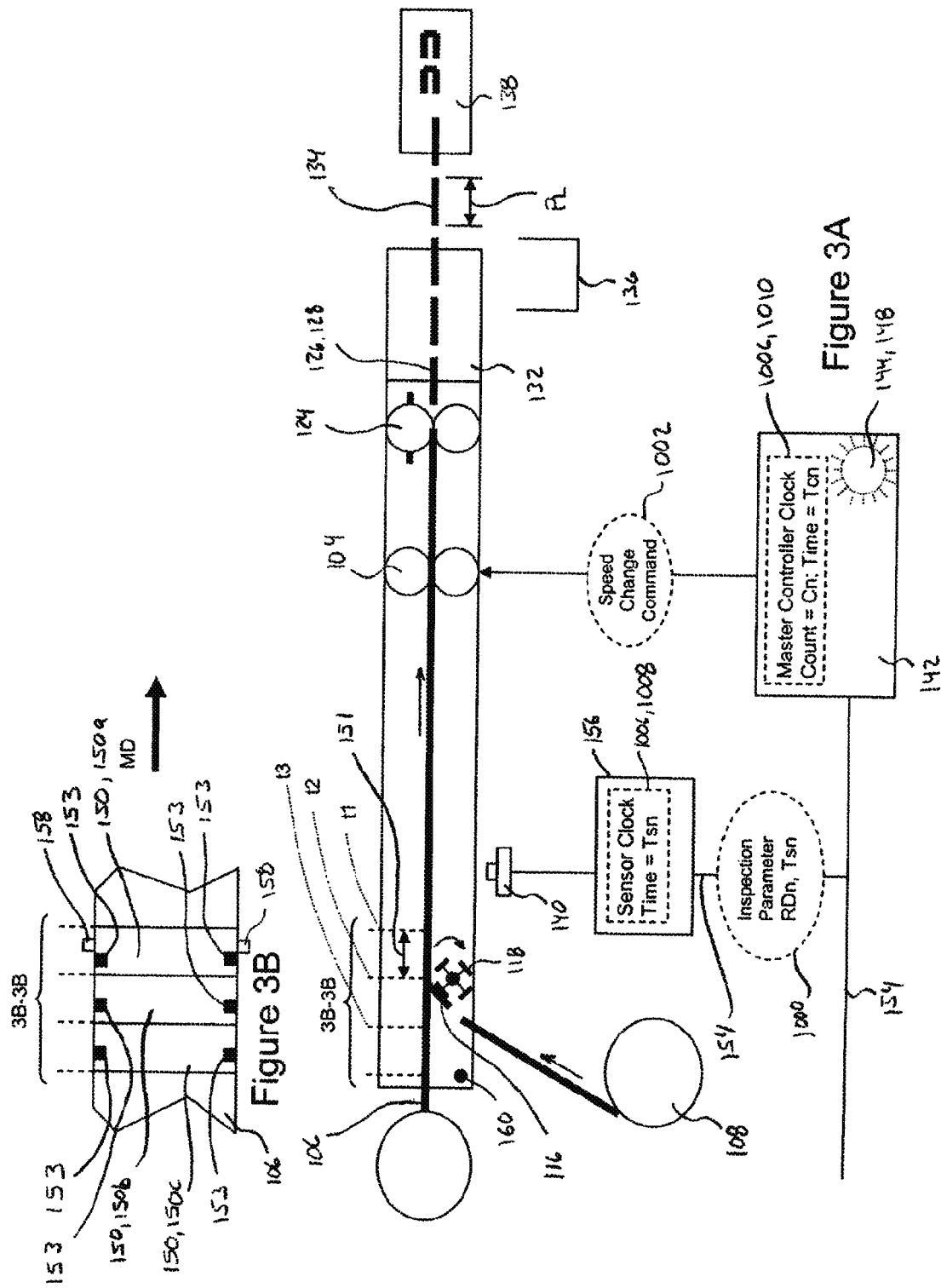
FIG. 3A is a schematic side view of a converting line, substrate, and components.
FIG. 3B is a top view of the substrates and components that corresponds with FIG. 3A.
Figure 4:
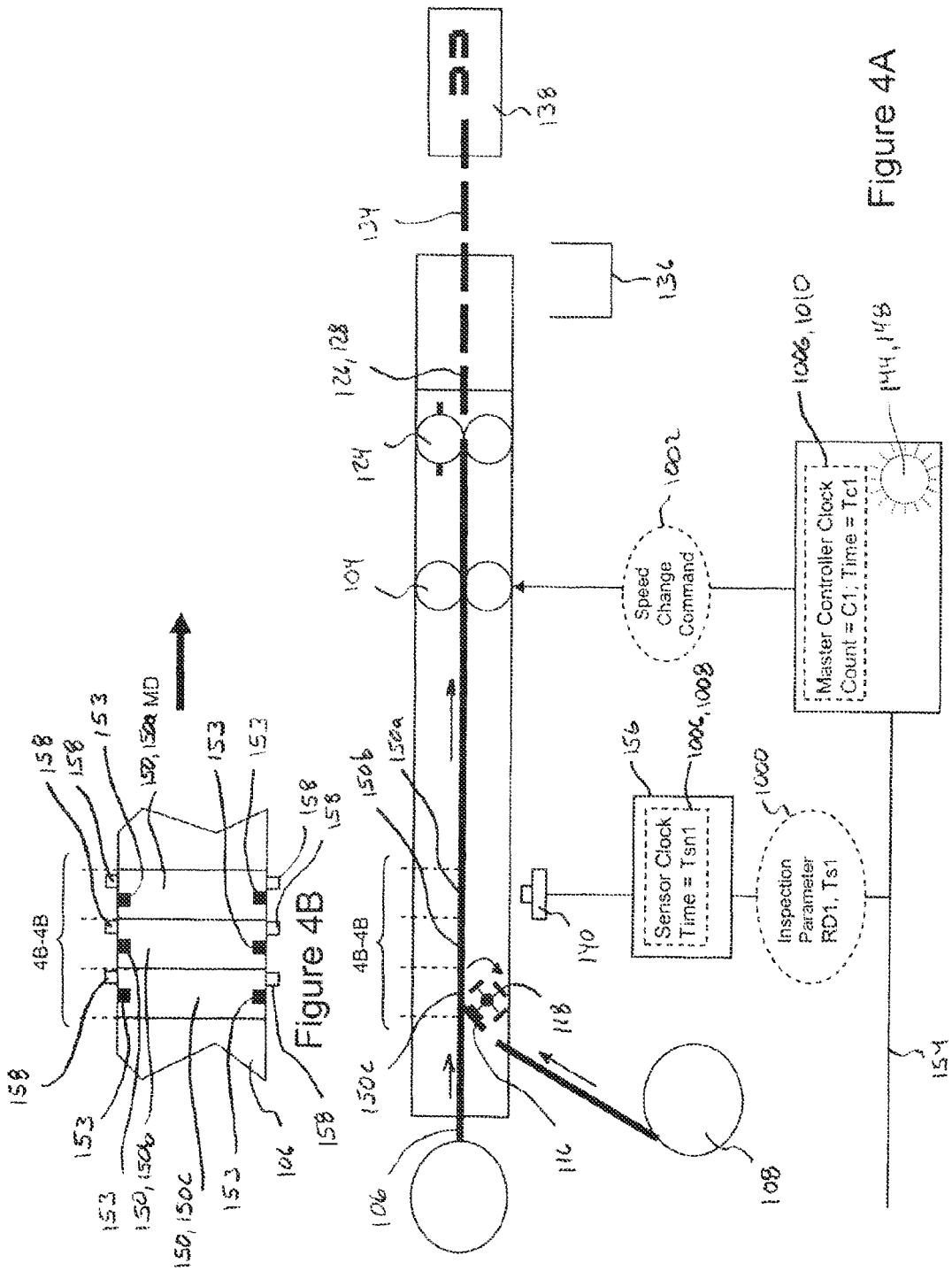
FIG. 4A is a schematic side view of a converting line, substrate, and components.
FIG. 4B is a top view of the substrates and components that corresponds with FIG. 4A.
Figure 5:
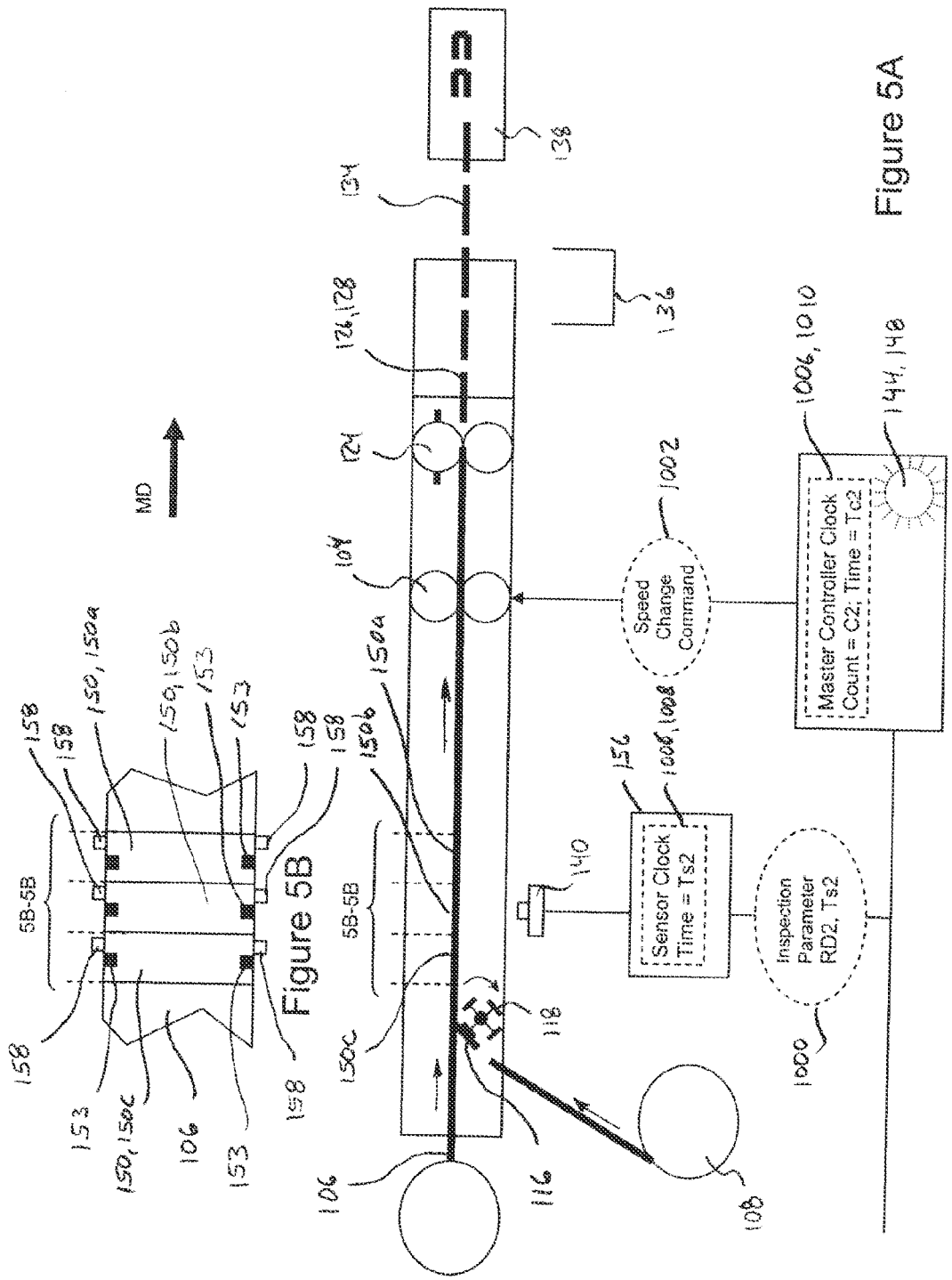
FIG. 5A is a schematic side view of a converting line, substrate, and components.
FIG. 5B is a top view of the substrates and components that corresponds with FIG. 5A.
Figure 6:
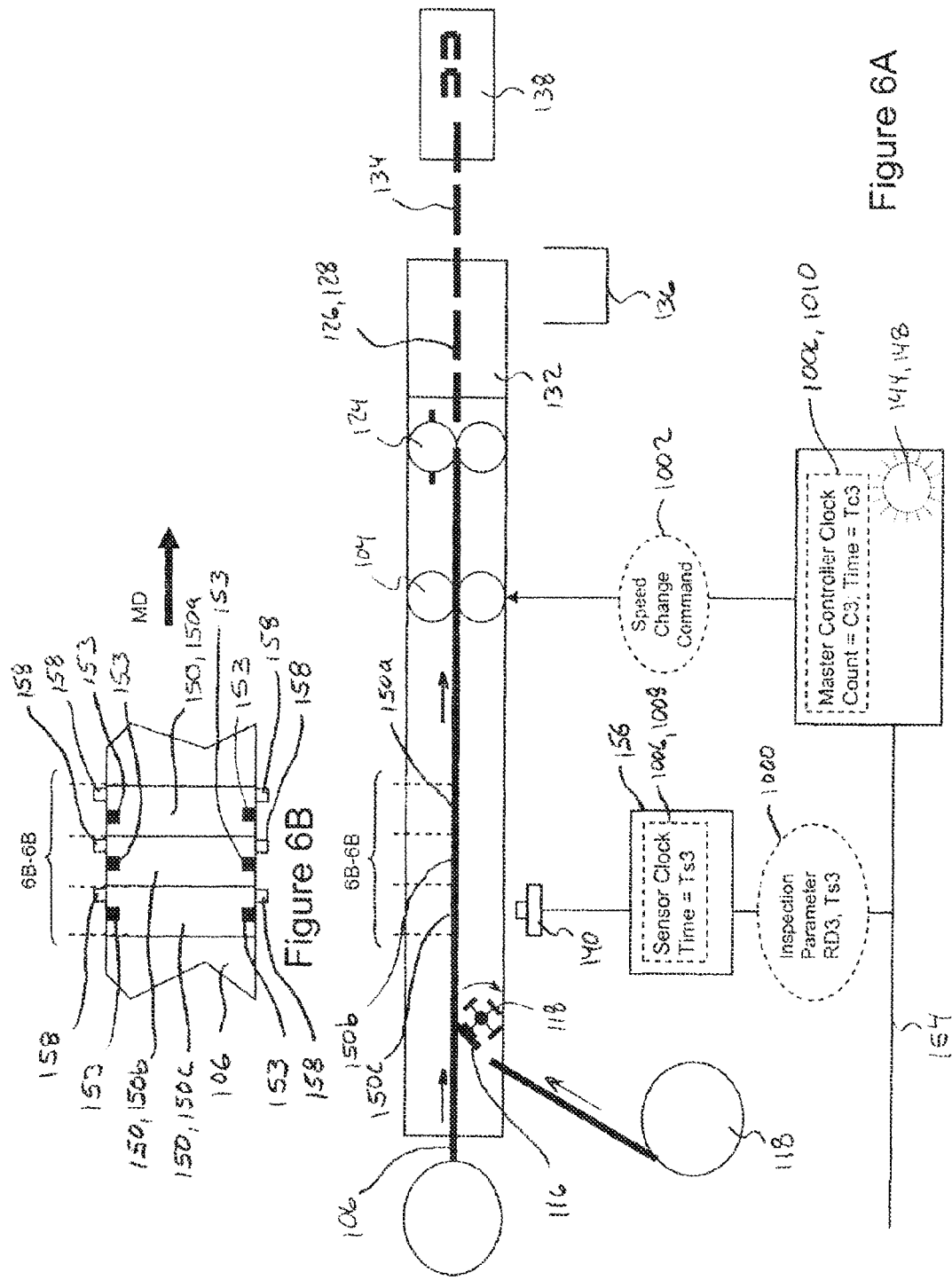
FIG. 6A is a schematic side view of a converting line, substrate, and components.
FIG. 6B is a top view of the substrates and components that corresponds with FIG. 6A.

As shown in FIGS. 3A-6B, the lengths 151 of the virtual products 150 in the machine direction correspond with the pitch lengths PL of products being produced. For the purposes of discussion, it is assumed that virtual product pitch length is 600 mm and the base web travels in the machine direction at a speed of 300 meters per minute, or 500 products per minute. In the present example, it is assumed that the virtual machine axis 148 is configured to generate counts simulating one complete one rotation that corresponds with a one pitch length advancement of the base substrate 106 in the machine direction. As such, one complete rotation of the machine axis 144 occurs every 120 milliseconds. Count data Cn is generated as the machine axis rotates. As discussed below, each count datum, Cn, includes a corresponding timestamp, Tcn. Upon each revolution of the machine axis 144, a shift register in the controller is incremented by one virtual product. For example, FIGS. 3A and 3B show the base substrate advancing in the machine direction past a reference point 160 in the converting line 100. At the reference point 160, a first virtual product 150a is present at the reference point at a first time, $t_1$. At a second time, $t_2$, 120 milliseconds after $t_1$, a second virtual product 150b is present at the same reference point 160, meanwhile the first virtual product 150a has progressed one pitch or 600 mm downstream in the machine direction. Continuing on, at a third time, $t_3$, 120 milliseconds after $t_2$, a third virtual product 150c is present at the same reference point 160, meanwhile the first and second virtual products 150a, 150b have progressed one pitch or 600 mm downstream in the machine direction. The aforementioned increments continue as the base substrate 106 moves through the converting line 100. FIGS. 3A and 3B also show the addition of a feature in the form of front ears 158 to the first virtual product 150a. Thus, the machine axis 144 generates count data and associated timestamps that correspond with desired or expected positions of the base substrate 106 along the converting line 100 as the base substrate advances in the machine direction.

FIGS. 4A and 4B show the advancement of the base substrate 106 in the machine direction past the inspection sensor 140. As discussed above, the inspection sensor 140 can be configured to detect the registration features 153 on the base substrate 106 and virtual products 150 passing thereby. As such, the inspection sensor 140 provides an inspection parameter 1000 to the communication network 154 via the remote I/O station 156, wherein the inspection parameter 1000 corresponds with the sensed presence of the registration features 153. When the position of the inspection sensor 140 along the converting line 100 is known by the controller 142, the controller 142 can correlate the inspection parameters 1000 provided by the inspection sensor 140 with the corresponding virtual products 150 based on the timestamps of the inspection parameters. More particularly, the controller 142 has a desired count datum from the machine axis 144 that corresponds with when a registration feature 153 is supposed to advance past the inspection sensor. If the registration feature 153 passes the inspection sensor 140 at the same time the desired count is generated, then the base substrate 106 and absorbent products 126 are being cut at the final knife 124 in the desired locations. However, if the registration feature 153 passes the inspection sensor 153 before or after the desired count is generated, then the controller 142 will adjust the speed of the base substrate 106 relative to the final knife 124 so that the base substrate 106 and absorbent products 126 are cut at the final knife 124 in the desired locations.

FIGS. 4A and 4B show the continued advancement from FIGS. 3A and 3B of the base substrate 106 in the machine direction, and in particular, advancement of the registration features 153 on the first virtual product 150a past the inspection sensor. FIG. 4A shows a first inspection parameter, RD1, having a corresponding timestamp, Ts1, being communicated to the communication network 154. RD1 is configured to provide an indication that the registration features 153 on the first virtual product 150a have been detected. As discussed below, RD1 may not be immediately received by the controller 142. Meanwhile, the machine axis 144 generates a count datum C1 at a time reported by master controller clock Tc1. For the purposes of this discussion, C1 is the count datum that corresponds with the setpoint location of the registration feature 153 on the first virtual product 150a.

Next, FIGS. 5A and 5B show the continued advancement from FIGS. 4A and 4B of the base substrate 106 in the machine direction, and in particular, advancement of the registration features 153 of the second virtual product 150b past the inspection sensor 140. FIG. 5A shows a second inspection parameter, RD2, having a corresponding timestamp, Ts2, being communicated to the communication network. RD2 provides an indication that the registration features on the second virtual product have been detected. Again, RD2 may not be immediately received by the controller 142 from the communication network 154. Meanwhile, the machine axis 144 generates a count datum C2 at a time reported by master controller clock Tc2. For the purposes of this discussion, C2 is the count datum that corresponds with the setpoint location of the registration feature 153 on the second virtual product 150b.

Next, FIGS. 6A and 6B show the continued advancement from FIGS. 5A and 5B of the base substrate 106 in the machine direction, and in particular, advancement of the registration features 153 of the third virtual product 150c past the inspection sensor 140. FIG. 6A shows a second inspection parameter, RD3, having a corresponding timestamp, Ts3, being communicated to the communication network 154. RD3 provides an indication that the registration features 153 on the third virtual product 150c have been detected. Again, RD3 may not be immediately received by the controller 142 from the communication network 154. Meanwhile, the machine axis 144 generates a count datum C3 at a time reported by master controller clock Tc3. For the purposes of this discussion, C3 is the count datum that corresponds with the setpoint location of the registration features 153 on the third virtual product 150c.

As previously mentioned, some amount of time may pass before the controller 142 receives the inspection parameters 1000 from the communication network 154. Such time delays may be the result of the non-deterministic nature of the Ethernet IP network. There may also be additional time before a controller analyzes the inspection parameters based on the controller's program cycle or loop time. However, notwithstanding such time delays, once the controller 142 receives and analyzes inspection parameters 1000, the controller can use the corresponding timestamps of the inspection parameters 1000 to compare the detection of the registration features 153 with the setpoint locations of the registration features on particular virtual products 150. For example, the controller 142 may receive and analyze RD1 at some time after RD1 was provided to the communication network 154. However, along with RD1, the controller will receive Ts1, which is provided by the sensor clock 1008. Because the sensor clock 1008 is synchronized with the master controller clock 1010, the controller 142 will be able to correlate RD1 with the count data generated by the machine axis 144. As discussed above, RD1 provides an indication of the detection of the registration features 153 on the first virtual product 150a with a time stamp, Ts1. Thus, the controller can compare the time Ts1 with the timestamp Tc1 associated with the count datum C1. If the timestamp Tc1 and Ts1 are within a desired range, the registration features 153 on the first virtual product 150a are passing the inspection sensor 140 at the correct time, and thus, the final knife 124 is cutting the base substrate 106 at the desired locations.

In another example, the controller 142 may receive and analyze RD2 at some time after RD2 was provided to the communication network. However, along with RD2, the controller will receive Ts2, which is provided by the sensor clock 1008. Because the sensor clock 1008 is synchronized with the master controller clock 1010, the controller 142 will be able to correlate RD2 with the count data generated by the machine axis 144. As discussed above, RD2 provides an indication of the detection of the registration features 153 on the second virtual product 150b with a time stamp, Ts2. Thus, the controller 142 can compare the time Ts2 with the timestamp Tc2 associated with the count datum C2. If the timestamp Ts2 indicates a time that occurred before Tc2, then the registration features 153 on the second virtual product 150b are passing the inspection sensor 140 before the desired time, and thus, the final knife 124 will not cut the base substrate 106 at the desired locations. Therefore, the controller 142 will send a speed change command 1002 to the converting line 100 to decrease the speed of the base substrate 106 relative to the final knife 124.

In yet another example, the controller 142 may receive and analyze RD3 at some time after RD3 was provided to the communication network 154. However, along with RD3, the controller 142 will receive Ts3, which is provided by the sensor clock 1008. Because the sensor clock 1008 is synchronized with the master controller clock 1010, the controller will be able to correlate RD3 with the count data generated by the machine axis 144. As discussed above, RD3 provides an indication of the detection of the registration features 153 on the third virtual product 150c with a time stamp, Ts3. Thus, the controller 142 can compare the time Ts3 with the timestamp Tc3 associated with the count datum C3. If the timestamp Ts3 indicates a time that occurred after Tc3, then the registration features 153 on the third virtual product 150c are passing the inspection sensor 140 after the desired time, and thus, the final knife 124 will not cut the base substrate 106 at the desired locations. Therefore, the controller 142 will send a speed change command 1002 to increase the speed of the base substrate 106 relative to the final knife 124.

Because the inspection parameters 1000 have timestamps provided from sensor clocks 1008 that are synchronized with the controller master clock 1010, the controller 142 can correlate the inspection parameters 1000 with the count data from the machine axis 144 without having to account for various system time delays, such as time delays in the communication network and controller loop times. In addition, the controller can be configured to account for time delays within the inspection sensor 140. As such when accounting for sensor time delays, the correlated location of the registration features 153 on the substrates and/or components may be accurate to within the accuracy of the sensor clock 1008 with respect to the controller master clock 1010. For example, the hardware and/or software configurations of an inspection sensor may create a time delay between the actual detection of a registration feature and the reporting of the inspection parameter onto the communication network. Such a sensor time delay can be accounted for in the controller by merely including an offset equal to the time delay when comparing the timestamps.

Expanding on the above discussion of the example provided in FIGS. 3A-6B, the estimated accuracies of the clocks 1008, 1010 and the speed of the substrate 106 in the machine direction can be used to determine a minimum length accuracy where registration features 153 are located on the virtual products 150. More particularly, the minimum length can be calculated by multiplying the estimated clock accuracy by the speed of the substrate. For example, where the clock accuracy meets the software implementation of IEE1588, the clocks may be assured to be accurate within 0.1 millisecond. Using the example speed above of 300 meters per minute, the virtual segment length in the machine direction is calculated to be 0.5 mm. In such a case, the position of a registration feature, such as corresponding with IS2 in the example above, may be known to within 0.5 mm in the machine direction MD on the base substrate.

As discussed above in the presented examples, the timestamp values corresponding with the detection of registration features and machine axis count values can be used by a controller to adjust the speed of advancing substrates and components to ensure the final knife cut is applied in the desired locations. In accordance with the present disclosure, it is to be further appreciated that the systems and methods above can be used to adjust the speed at which components are combined with other components and/or substrates.

In accordance with the present disclosure, it is to be further appreciated that the inspection sensor can be configured to provide various types of inspection parameters that may be utilized by the controller in various ways. In one scenario, the inspection sensor can be configured to detect the relative positions of components added to an advancing substrate, and based on the sensed relative positions, adjust the speed at which the components are added to the substrate. For example, with reference to FIGS. 3A and 3B, the inspection sensor may be configured to detect the positions of the front ears added to the base substrate relative to a physical or virtual reference on the base substrate. Based on the sensed positions, the controller can adjust the speed at which the auxiliary substrate advances relative to the base substrate.

As previously mentioned, the systems and methods herein may be used to monitor various types of substrates and components during the manufacture of various different products. For the purposes of a specific illustration, FIG. 7 shows one example of a disposable absorbent article 750, such as described in U.S. Patent Publication No. US2008/0132865 A1, in the form of a diaper 752 that may be constructed from substrates and components monitored according to the systems and methods disclosed herein. In particular, FIG. 7 is a plan view of one embodiment of a diaper 752 including a chassis 754 shown in a flat, unfolded condition, with the portion of the diaper 752 that faces a wearer oriented towards the viewer. A portion of the chassis structure is cut-away in FIG. 7 to more clearly show the construction of and various features that may be included in embodiments of the diaper.

As shown in FIG. 7, the diaper 752 includes a chassis 754 having a first ear 756, a second ear 758, a third ear 760, and a fourth ear 762. To provide a frame of reference for the present discussion, the chassis is shown with a longitudinal axis 764 and a lateral axis 766. The chassis 754 is shown as having a first waist region 768, a second waist region 770, and a crotch region 772 disposed intermediate the first and second waist regions. The periphery of the diaper is defined by a pair of longitudinally extending side edges 774, 776; a first outer edge 778 extending laterally adjacent the first waist region 768; and a second outer edge 780 extending laterally adjacent the second waist region 770. As discussed above, the pitch length, PL, of the absorbent article 750 may be defined by the distance between the first outer edge 778 and the second outer edge 780. As shown in FIG. 7, the chassis 754 includes an inner, body-facing surface 782, and an outer, garment-facing surface 784. A portion of the chassis structure is cut-away in FIG. 7 to more clearly show the construction of and various features that may be included in the diaper. As shown in FIG. 7, the chassis 754 of the diaper 752 may include an outer covering layer 786 including a topsheet 788 and a backsheet 790. An absorbent core 792 may be disposed between a portion of the topsheet 788 and the backsheet 790. As discussed in more detail below, any one or more of the regions may be stretchable and may include an elastomeric material or laminate as described herein. As such, the diaper 752 may be configured to adapt to a specific wearer's anatomy upon application and to maintain coordination with the wearer's anatomy during wear.

As previously mentioned, the chassis 754 of the diaper 752 may include the backsheet 790, shown for example, in FIG. 7. In some embodiments, the backsheet is configured to prevent exudates absorbed and contained within the chassis from soiling articles that may contact the diaper, such as bedsheets and undergarments. Some embodiments of the backsheet may be fluid permeable, while other embodiments may be impervious to liquids (e.g., urine) and comprises a thin plastic film. Some backsheet films may include those manufactured by Tredegar Industries Inc. of Terre Haute, Ind. and sold under the trade names X15306, X10962, and X10964. Other backsheet materials may include breathable materials that permit vapors to escape from the diaper while still preventing exudates from passing through the backsheet. Exemplary breathable materials may include materials such as woven webs, nonwoven webs, composite materials such as film-coated nonwoven webs, and microporous films. Suitable breathable composite materials are described in greater detail in PCT Application No. WO 95/16746, published on Jun. 22, 1995 in the name of E. I. DuPont and U.S. Pat. No. 5,865,823, both of which are hereby incorporated by reference herein. Other breathable backsheets including nonwoven webs and apertured formed films are described in U.S. Pat. Nos. 5,571,096 and 6,573,423, which are all hereby incorporated by reference herein.

The backsheet 790, or any portion thereof, may be stretchable in one or more directions. In one embodiment, the backsheet may comprise a structural elastic-like film ("SELF") web. Embodiments of SELF webs are more completely described in U.S. Pat. Nos. 5,518,801; 5,723,087; 5,691,035; 5,916,663; and 6,027,483, which are all hereby incorporated by reference herein. In some embodiments, the backsheet may comprise elastomeric films, foams, strands, nonwovens, or combinations of these or other suitable materials with nonwovens or synthetic films. Additional embodiments include backsheets that comprise a stretch nonwoven material; an elastomeric film in combination with an extensible nonwoven; an elastomeric nonwoven in combination with an extensible film; and/or combinations thereof. Details on such backsheet embodiments are more completely described in U.S. Publication Nos. US2007/0287348A1; US2007/0287982A1; and US2007/0287983A1, which are all hereby incorporated by reference herein. The backsheet 790 may be joined with the topsheet 788, the absorbent core 792, and/or other elements of the diaper 752 in various ways. For example, the backsheet may be connected with a uniform continuous layer of adhesive, a patterned layer of adhesive, or an array of separate lines, spirals, or spots of adhesive. One embodiment utilizes an open pattern network of filaments of adhesive as disclosed in U.S. Pat. No. 4,573,986, which is hereby incorporated by reference herein. Other embodiments utilize several lines of adhesive filaments which are swirled into a spiral pattern, as is illustrated by the apparatus and methods shown in U.S. Pat. Nos. 3,911,173; 4,785,996; and 4,842,666, which are all hereby incorporated by reference herein. In some embodiments, the backsheet is connected with heat bonds, pressure bonds, ultrasonic bonds, dynamic mechanical bonds, or any other suitable attachment means or a combination thereof.

The topsheet 788 may be constructed to be compliant, soft feeling, and non-irritating to the wearer's skin. Further, all or at least a portion of the topsheet 788 may be liquid pervious, permitting liquid to readily penetrate therethrough. As such, the topsheet may be manufactured from a wide range of materials, such as porous foams; reticulated foams; apertured nonwovens or plastic films; or woven or nonwoven webs of natural fibers (e.g., wood or cotton fibers), synthetic fibers (e.g., polyester or polypropylene fibers), or a combination of natural and synthetic fibers. One example of a topsheet including a web of staple length polypropylene fibers is manufactured by Veratec, Inc., a Division of International Paper Company, of Walpole, Mass. under the designation P-8. Examples of formed film topsheets are described in U.S. Pat. Nos. 3,929,135; 4,324,246; 4,342,314; 4,463,045; and 5,006,394, all of which are hereby incorporated by reference herein. Other topsheets may be made in accordance with U.S. Pat. Nos. 4,609,518 and 4,629,643, both of which are hereby incorporated by reference herein.

In some embodiments, the topsheet 788 is made of a hydrophobic material or is treated to be hydrophobic in order to isolate the wearer's skin from liquids contained in the absorbent core. If the topsheet is made of a hydrophobic material, at least the upper surface of the topsheet may be treated to be hydrophilic so that liquids will transfer through the topsheet more rapidly. The topsheet can be rendered hydrophilic by treating it with a surfactant or by incorporating a surfactant into the topsheet. A more detailed discussion of such a treatment and hydrophilicity is contained in U.S. Pat. Nos. 4,988,344 and 4,988,345, all of which are hereby incorporated by reference herein. A more detailed discussion of some methods for incorporating surfactant in the topsheet can be found in U.S. Statutory Invention Registration No. H1670, which was published on Jul. 1, 1997, in the names of Aziz et al., all of which are hereby incorporated by reference herein. In some embodiments, the topsheet 788 may include an apertured web or film that is hydrophobic. This may be accomplished eliminating the hydrophilizing treatment step from the production process and/or applying a hydrophobic treatment to the topsheet, such as a polytetrafluoroethylene compound like SCOTCHGUARD or a hydrophobic lotion composition, as described below. A more detailed discussion of various apertured topsheets can be found in U.S. Pat. Nos. 5,342,338; 5,941,864; 6,010,491; and 6,414,215, all of which are hereby incorporated by referenced herein.

The absorbent core 792 may include absorbent material that is generally compressible, conformable, non-irritating to the wearer's skin, and capable of absorbing and retaining liquids such as urine and other body exudates. The absorbent core 792 can also be manufactured in a wide variety of sizes and shapes (e.g., rectangular, hourglass, T-shaped, asymmetric, etc.). The absorbent core may also include a wide variety of liquid-absorbent materials commonly used in disposable diapers and other absorbent articles. In one example, the absorbent core includes comminuted wood pulp, which is generally referred to as airfelt. Examples of other absorbent materials include creped cellulose wadding; meltblown polymers, including coform; chemically stiffened, modified or cross-linked cellulosic fibers; tissue, including tissue wraps and tissue laminates; absorbent foams; absorbent sponges; superabsorbent polymers; absorbent gelling materials; or any other known absorbent material or combinations of materials. Exemplary absorbent structures are described in U.S. Pat. Nos. 4,610,678; 4,673,402; 4,834,735; 4,888,231; 5,137,537; 5,147,345; 5,342,338; 5,260,345; 5,387,207; and 5,650,222, all of which are hereby incorporated by reference herein.

The absorbent core 792 may also have a multiple layered construction. A more detailed discussion of various types of multi-layered absorbent cores can be found in U.S. Pat. Nos. 5,669,894; 6,441,266; and 5,562,646; European Patent No. EP0565606B1; U.S. Patent Publication No. 2004/0162536A1; 2004/0167486A1; and PCT Publication No. WO 2006/015141, which are all hereby incorporated by reference herein. In some embodiments, the absorbent article includes an absorbent core that is stretchable. In such a configuration, the absorbent core may be adapted to extend along with other materials of the chassis in longitudinal and/or lateral directions. The absorbent core can also be connected with the other components of the chassis various ways. For example, the diaper may include a "floating core" configuration or a "bucket" configuration wherein the diaper includes an anchoring system that can be configured to collect forces tending to move the article on the wearer. The absorbent article may also include an elastic waist feature 702 shown in FIG. 7 in the form of a waist band 794 and may provide improved fit and waste containment. The elastic waist feature 702 may be configured to elastically expand and contract to dynamically fit the wearer's waist. The elastic waist feature 702 can be incorporated into the diaper in accordance with the methods discussed herein and may extend at least longitudinally outwardly from the absorbent core 792 and generally form at least a portion of the first and/or second outer edges 778, 780 of the diaper 752. In addition, the elastic waist feature may extend laterally to include the ears. While the elastic waist feature 702 or any constituent elements thereof may comprise one or more separate elements affixed to the diaper, the elastic waist feature may be constructed as an extension of other elements of the diaper, such as the backsheet 790, the topsheet 788, or both the backsheet and the topsheet. In addition, the elastic waist feature 702 may be disposed on the outer, garment-facing surface 784 of the chassis 754; the inner, body-facing surface 782; or between the inner and outer facing surfaces. The elastic waist feature 702 may be constructed in a number of different configurations including those described in U.S. Patent Publication Nos. 2007/0142806; 2007/0142798; and 2007/0287983, all of which are hereby incorporated by reference herein.

Although the first and second ears 756, 158 as well as the third and fourth ears 760, 762 shown in FIG. 7 are illustrated as being integrally formed with the chassis 754, it is to be appreciated that other embodiments may include ears that are discrete elements connected with the chassis. In some embodiments, the ears are configured to be stretchable. The ears may also include one or more fastener elements adapted to releasably connect with each other and/or other fastener elements on the chassis. A more detailed discussion of stretchable ears can be found in U.S. Pat. Nos. 4,857,067; 5,151,092; 5,674,216; 6,677,258; 4,381,781; 5,580,411; and 6,004,306, which are all hereby incorporated by reference herein. The ears may also include various geometries and arrangements of stretch zones or elements, such as discussed in U.S. Pat. Publication Nos. US2005/0215972A1 and US2005/0215973A1, which are all hereby incorporated by reference herein.

As shown in FIG. 7, the diaper 752 may include leg cuffs 796 that may provide improved containment of liquids and other body exudates. The leg cuffs 796 may be disposed in various ways on the diaper 752. For example, the leg cuffs 796 may be disposed on the outer, garment-facing surface 784 of the chassis 754; the inner, body-facing surface 782; or between the inner and outer facing surfaces. Leg cuffs 796 may also be referred to as leg bands, side flaps, barrier cuffs, or elastic cuffs. U.S. Pat. No. 3,860,003, which is hereby incorporated by reference herein, describes a disposable diaper that provides a contractible leg opening having a side flap and one or more elastic members to provide an elasticized leg cuff (a gasketing cuff). U.S. Pat. Nos. 4,808,178 and 4,909,803, which are both hereby incorporated by reference herein, describe disposable diapers having "stand-up" elasticized flaps (barrier cuffs). U.S. Pat. Nos. 4,695,278 and 4,795,454, which are both hereby incorporated by reference herein, describe disposable diapers having dual cuffs, including gasketing cuffs and barrier cuffs. In some embodiments, it may be desirable to treat all or a portion of the leg cuffs with a lotion, as described above. In addition to leg cuffs, diaper can also include an elastic gasketing cuff with one or more elastic strands positioned outboard of the barrier cuff. The leg cuffs may be treated with a hydrophobic surface coating, such as described in U.S. Pat. Publication No. 20060189956A1, which is hereby incorporated by reference herein.

The diaper 752 may be provided in the form of a pant-type diaper or may alternatively be provided with a re-closable fastening system, which may include fastener elements in various locations to help secure the diaper in position on the wearer. For example, fastener elements may be located on the first and second ears and may be adapted to releasably connect with one or more corresponding fastening elements located in the second waist region. It is to be appreciated that various types of fastening elements may be used with the diaper. In one example, the fastening elements include hook & loop fasteners, such as those available from 3M or Velcro Industries. In other examples, the fastening elements include adhesives and/or tap tabs, while others are configured as a macrofastener or hook (e.g., a MACRO or "button-like" fastener). Some exemplary fastening elements and systems are disclosed in U.S. Pat. Nos. 3,848,594; 4,662,875; 4,846,815; 4,894,060; 4,946,527; 5,151,092; and 5,221,274, which are all hereby incorporated by reference herein. Additional examples of fasteners and/or fastening elements are discussed in U.S. Pat. Nos. 6,251,097 and 6,432,098; and U.S. Patent Publication Nos. 2007/0078427 and 2007/0093769, which are all hereby incorporated by reference herein. Other fastening systems are described in more detail in U.S. Pat. Nos. 5,595,567; 5,624,427; 5,735,840; and 5,928,212, which are all hereby incorporated by reference herein. The fastening system may also provide a means for holding the article in a disposal configuration as disclosed in U.S. Pat. No. 4,963,140, which is hereby incorporated by reference herein.

It is to be appreciated that the methods and systems disclosed herein may be utilized to monitor the quality of substrates and components as well as respective placements of substrates and/or components during the manufacture of absorbent articles, such as for example, topsheets, backsheets, absorbent cores, ears, waist features, and graphics printed thereon. It is also to be appreciated that the registration systems and methods described herein may also be utilized in combination with other types of control systems and methods, such as described in U.S. patent application Ser. No. 12/476,479, entitled "SYSTEMS AND METHODS FOR CONTROLLING PHASING OF ADVANCING SUBSTRATES IN ABSORBENT ARTICLE CONVERTING LINES," filed on Jun. 2, 2009, and U.S. patent application Ser. No. 12/476,553, entitled "SYSTEMS AND METHODS FOR DETECTING AND REJECTING DEFECTIVE ABSORBENT ARTICLES FROM A CONVERTING LINE," filed on Jun. 2, 2009. Further, the time synchronization features of the methods and systems described herein may be utilized in other types of control systems and methods such as for example: data storage and correlation methods with repeat application devices and multiple application stations such as described in U.S. Pat. No. 6,829,516; raw material database integration such as described in U.S. Pat. No. 7,162,319; web guide control methods and systems such as described in U.S. Pat. No. 6,801,828; and data mining and trending methods and systems such as described in U.S. Pat. No. 6,845,278.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method for registering absorbent products from a web converting manufacturing process, the method comprising the steps of:
providing a communication network;
connecting a sensor with the communication network, the sensor including a sensor clock;
connecting a controller with the communication network, the controller including a controller clock;
synchronizing the sensor clock with the controller clock such that the reported time of the controller clock and the sensor clock are correlated;
advancing a substrate in a machine direction through a converting process at a first speed;
sequentially adding component parts to the substrate at a second speed;
providing a machine axis that generates counts that correspond with locations along machine direction;
assigning a timestamp to each count, wherein each timestamp is based on the controller clock;
detecting positions of the component parts with the sensor;
communicating component part position detections from the sensor to the communication network;
assigning a timestamp to each component part position detection, wherein each timestamp is based on the sensor clock;
receiving the component part position detections and corresponding timestamps from the communication network into the controller;
comparing the timestamps of the component part position detections with the timestamps of the count data;
adjusting the second speed based on the comparison of the timestamps associated with the component part position detections with the timestamps associated with the count data;
cutting the substrate with component parts added thereto into discrete absorbent articles; and
packaging the discrete absorbent articles.

2. The method of claim 1, further comprising the step of adjusting the timestamps associated with the component part position detections based on a sensor time delay.

3. The method of claim 1, wherein the component parts include parts added as a continuous web of material and parts added as a discontinuous web of material.

4. The method of claim 1, wherein the communication network is non-deterministic.

5. The method of claim 1, wherein the machine axis is a virtual axis.

6. The method of claim 1, wherein the absorbent articles are diapers.

7. The method of claim 6, wherein the first substrate forms backsheets of the diapers.

* * * * *